(12) United States Patent  
Asafusa et al.

(10) Patent No.: US 9,089,874 B2  
(45) Date of Patent: Jul. 28, 2015

(54) ULTRASONIC DIAGNOSTIC APPARATUS AND ULTRASONIC PROBE

(75) Inventors: Katsunori Asafusa, Tokyo (JP); Shinichiro Kishi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 601 days.

(21) Appl. No.: 12/808,101

(22) PCT Filed: Dec. 10, 2008

(86) PCT No.: PCT/JP2008/072383

§ 371 (c)(1),  
(2), (4) Date: Jun. 14, 2010

(87) PCT Pub. No.: WO2009/075280

PCT Pub. Date: Jun. 18, 2009

(65) Prior Publication Data

US 2010/0268081 A1    Oct. 21, 2010

(30) Foreign Application Priority Data

Dec. 13, 2007    (JP) ................................. 2007-321718

(51) Int. Cl.
*A61B 8/00* (2006.01)  
*B06B 1/02* (2006.01)

(52) U.S. Cl.
CPC .............. *B06B 1/0292* (2013.01); *A61B 8/4483* (2013.01); *A61B 8/00* (2013.01)

(58) Field of Classification Search
CPC ....... B06B 1/0292; A61B 8/4483; A61B 8/00  
USPC ........................................................ 600/437  
See application file for complete search history.

(56) References Cited

U.S. PATENT DOCUMENTS

| | | | | |
|---|---|---|---|---|
| 4,763,068 | A | * | 8/1988 | Schmitt et al. ................ 324/126 |
| 5,416,357 | A | * | 5/1995 | Kobayashi et al. ........... 257/536 |

(Continued)

FOREIGN PATENT DOCUMENTS

| | | |
|---|---|---|
| JP | 3-080841 | 4/1991 |
| JP | 2002-530145 | 9/2002 |

(Continued)

OTHER PUBLICATIONS

"Influence of the Electrode Size and Location on the Performance of a CMUT" by B. Bayram, et al., 2001 IEEE Ultrasonics Symposium, pp. 949-952.
"Calculation and Measurement of Electromechanical Coupling Coefficient of Capacitive Micromachined Ultrasonic Transducers" by G. Yaralioglu, et al., IEEE, vol., 50, No. 4, Apr. 2003, pp. 449-456.

*Primary Examiner* — Bo J Peng  
(74) *Attorney, Agent, or Firm* — Brundidge & Stanger, P.C.

(57) ABSTRACT

An ultrasonic diagnosis apparatus including an ultrasonic probe having plural vibrating elements whose electromechanical coupling coefficients vary in accordance with the magnitude of a bias voltage supplied from a bias voltage supply unit, an ultrasonic image constructing unit for constructing an ultrasonic image on the basis of a reflection echo signal received from the ultrasonic probe, and a display unit for displaying the ultrasonic image is equipped with a calculation unit for calculating the magnitude of the bias voltage with respect to a collapse voltage of the vibrating elements, a storage unit for storing the calculated magnitude of the bias voltage, and a control unit for making the bias voltage supply unit supply the bias voltage to the vibrating elements in accordance with the stored magnitude of the bias voltage.

17 Claims, 13 Drawing Sheets

(56) References Cited

U.S. PATENT DOCUMENTS

| | | | |
|---|---|---|---|
| 2005/0219953 A1* | 10/2005 | Bayram et al. | 367/178 |
| 2006/0173342 A1* | 8/2006 | Panda et al. | 600/459 |
| 2006/0279174 A1* | 12/2006 | Oliver et al. | 310/338 |
| 2007/0016020 A1* | 1/2007 | Oshiki et al. | 600/437 |
| 2008/0075306 A1* | 3/2008 | Poulsen et al. | 381/111 |

FOREIGN PATENT DOCUMENTS

| | | | | |
|---|---|---|---|---|
| WO | WO 2007055320 A1 * | 5/2007 | | A61B 8/00 |
| WO | WO 2007058056 A1 * | 5/2007 | | A61B 8/00 |

* cited by examiner

ULTRASONIC DIAGNOSTIC APPARATUS AND ULTRASONIC PROBE

TECHNICAL FIELD

The present invention relates to an ultrasonic diagnosis apparatus for picking up an ultrasonic image by using an ultrasonic probe using cMUT (capacitive Micromachined Ultrasonic Transducer) chip.

BACKGROUND ART

An ultrasonic diagnosis apparatus transmits an ultrasonic wave to an examinee through an ultrasonic probe and picks up an ultrasonic image on the basis of a reflection echo signal output from the ultrasonic probe. A cMUT chip as disclosed in Patent Document 1 has been recently adopted for the ultrasonic probe. The cMUT chip is an ultrafine capacitance type ultrasonic transducer manufactured by a semiconductor micro-fabrication process, and it has a characteristic that an electromechanical coupling coefficient varies in accordance with a bias voltage value which is superposed on a driving signal supplied from an ultrasonic transceiver and applied.

Furthermore, Patent Document 2 discloses an ultrasonic diagnosis apparatus in which ultrasonic probe construction information such as an arrangement interval between transducers of an ultrasonic probe, curvature, focal point, aperture is stored in a memory of the ultrasonic probe.

Patent Document 1: JP-A-2006-20313
Patent Document 2: JP-A-63-154160

DISCLOSURE OF THE INVENTION

Problem to be Solved by the Invention

However, the above Patent Document 1 merely discloses the ultrasonic probe using the cMUT chip, and the Patent Document 2 merely discloses the ultrasonic probe having the memory for storing information on an arrangement condition of the transducers. Therefore, they do not raise any problem concerning reduction in sensitivity of the ultrasonic probe due to a collapse state of the cMUT chip.

Here, the collapse state is a state that when an applied bias voltage is equal to some voltage, the center portion of a film body of an vibrating element (containing an upper electrode) comes into contact with the surface of a lower electrode, charge transfer from the lower electrode to the upper electrode occurs, and the sensitivity of the vibrating element, that is, the ultrasonic probe is reduced due to the effect of the charge transfer. A voltage occurring due to the charge transfer under the collapse state will be referred to as a collapse voltage.

An object of the invention is to provide an ultrasonic diagnosis apparatus and an ultrasonic probe that can suppress sensitivity reduction of the ultrasonic probe.

Means of Solving the Problem

An ultrasonic diagnosis apparatus according to the invention has the following constituent elements.

(1) An ultrasonic diagnosis apparatus having an ultrasonic probe having plural vibrating elements whose electromechanical coupling coefficients vary in accordance with the magnitude of a bias voltage supplied from a bias voltage supply unit, an ultrasonic image constructing unit for constructing an ultrasonic image on the basis of a reflection echo signal received from the ultrasonic probe, and a display unit for displaying the ultrasonic image, is characterized by comprising: a calculation unit for calculating the magnitude of the bias voltage with respect to the collapse voltage of the vibrating element, a storage unit for storing the calculated magnitude of the bias voltage, and a control unit for making the bias voltage supply unit supply the bias voltage to the vibrating elements in accordance with the stored magnitude of the bias voltage.

(2) An ultrasonic diagnosis apparatus having an ultrasonic probe having plural vibrating elements whose electromechanical coupling coefficients vary in accordance with the magnitude of a bias voltage supplied from a bias voltage supply unit, an ultrasonic image constructing unit for constructing an ultrasonic image on the basis of a reflection echo signal received from the ultrasonic probe, and a display unit for displaying the ultrasonic image, is characterized by comprising: a storage unit for storing a collapse voltage of the vibrating elements, and a control unit for calculating the magnitude of the bias voltage on the basis of the collapse voltage read out from the storage unit, and making the bias voltage supply unit supply the bias voltage to the vibrating elements in accordance with the magnitude of the bias voltage.

(3) An ultrasonic diagnosis apparatus having an ultrasonic probe having plural vibrating elements whose electromechanical coupling coefficients vary in accordance with the magnitude of a bias voltage supplied from a bias voltage supply unit, an ultrasonic image constructing unit for constructing an ultrasonic image on the basis of a reflection echo signal received from the ultrasonic probe, and a display unit for displaying the ultrasonic image, is characterized by comprising: a measuring unit for measuring a collapse voltage of the vibrating elements of the ultrasonic probe, a calculation unit for calculating the magnitude of a bias voltage which is equal to or less than the collapse voltage, a storage unit for storing the calculated bias voltage, and a control unit for making the bias voltage supply unit supply the bias voltage to the vibrating elements in accordance with the magnitude of the bias voltage.

The ultrasonic probe according to the invention has the following constitute elements.

(1) An ultrasonic probe having plural vibrating elements whose electromechanical coupling coefficients vary in accordance with a bias voltage supplied from a bias voltage supply unit, and a storage unit for storing information concerning the vibrating elements, is characterized by further comprising a calculation unit for calculating the magnitude of the bias voltage to a collapse voltage of the vibrating elements, wherein the storage unit stores the magnitude of the bias voltage of the vibrating units and enables the magnitude of a bias voltage read out from the storage unit to be output to the bias voltage supply unit.

(2) An ultrasonic probe having plural vibrating elements whose electromechanical coupling coefficients vary in accordance with a bias voltage supplied from a bias voltage supply unit, and a storage unit for storing information concerning the vibrating elements, is characterized in that the storage unit stores a collapse voltage of the vibrating elements and the ultrasonic probe further comprises a calculation unit for calculating the magnitude of a bias voltage from the collapse voltage read out from the storage unit.

(3) An ultrasonic probe having plural vibrating elements whose electromechanical coupling coefficients vary in accordance with a bias voltage supplied from a bias voltage supply unit, and a storage unit for storing information concerning the vibrating elements, is characterized by further comprising a calculation unit for calculating the magnitude of the bias voltage which is equal to or less than a collapse voltage of the vibrating elements, wherein the storage unit stores the magnitude of the bias voltage of the vibrating elements, and enables the magnitude of a bias voltage read out from the storage unit to be output to the bias voltage supply unit.

Effect of the Invention

According to the invention, there can be provided an ultrasonic diagnosis apparatus and an ultrasonic probe that can suppress sensitivity reduction of the ultrasonic probe.

BRIEF DESCRIPTION OF THE DRAWINGS

DESCRIPTION OF REFERENCE NUMERALS 1 ultrasonic diagnosis apparatus, 2 ultrasonic probe, 3 memory, 4 transmission unit, 5 calculation unit, 6 bias voltage supply unit, 7 transmission/reception separating unit, 8 reception unit, 9 capacitance measuring unit, 10 phasing and adding unit, 12 image processing unit, 14 display unit, 16 control unit, 18 operation unit Best Mode For Carrying Out The Invention An ultrasonic diagnosis apparatus 1 and an ultrasonic probe 2 to which the invention is applied will be described with reference to the drawings. FIG. 1 is a block diagram showing the ultrasonic diagnosis apparatus 1 according to an embodiment of the invention.

As shown in FIG. 1, the ultrasonic diagnosis apparatus 1 comprises an ultrasonic probe 2, a memory 3, a transmission unit 4, a calculation unit 5, a bias voltage supply unit 6, a transmission/reception separating unit 7, a reception unit 8, a capacitance measuring unit 9, a phasing and adding unit 10, an image processing unit 12, a display unit 14, a control unit 16 and an operation unit 18.

Figure 1:
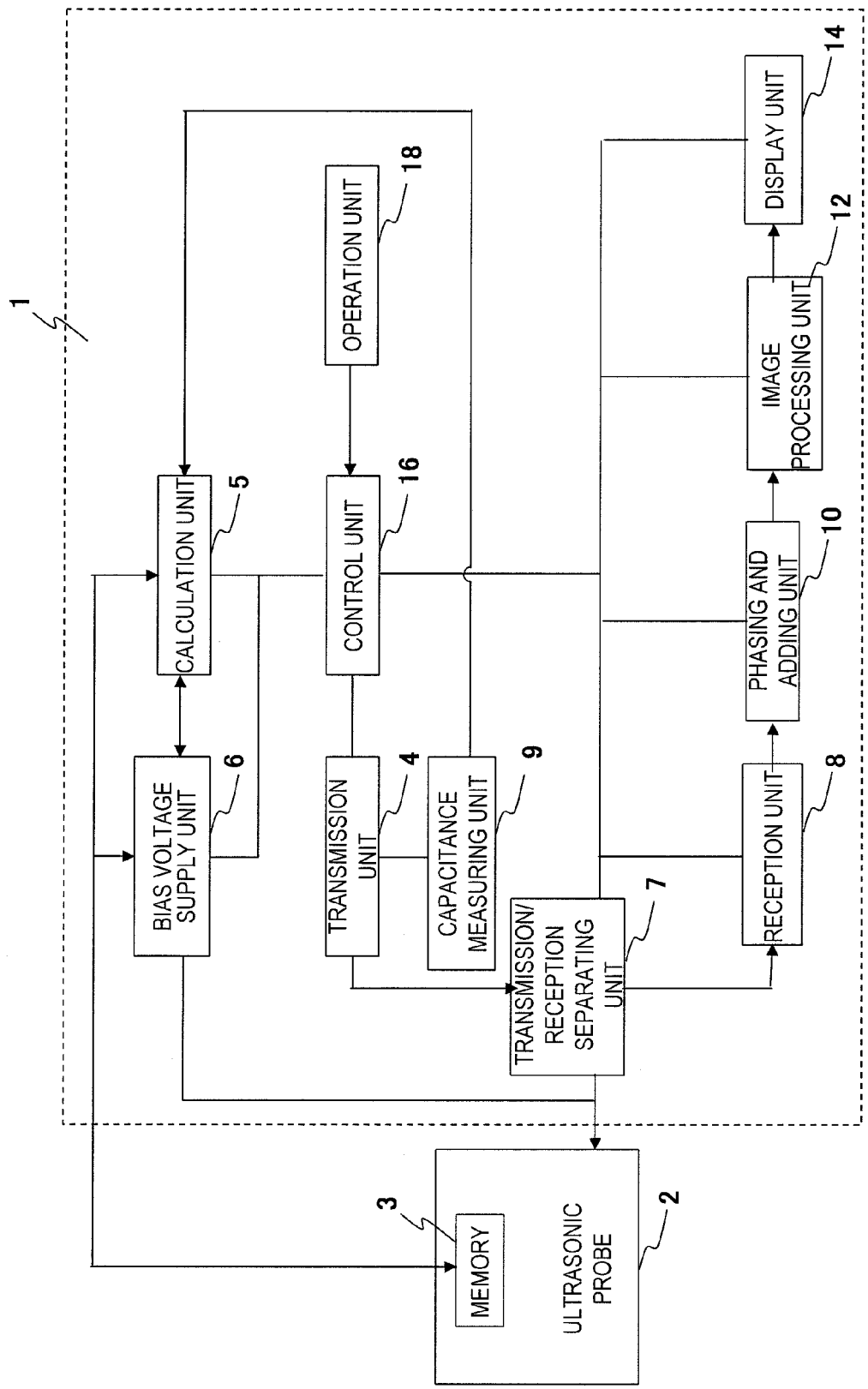
FIG. 1 is a diagram showing the overall construction of the invention.

The ultrasonic probe 2 is brought into contact with an examinee to transmit/receive an ultrasonic wave to/from the examinee. An ultrasonic wave is emitted from the ultrasonic probe 2 to the examinee, and a reflection echo signal generated from the examinee is received by the ultrasonic probe 2.

A driving signal is supplied to the ultrasonic probe 2 by using the transmission unit 4 and the bias voltage supply unit 6, the reception unit 8 receives the reflection echo signal output from the ultrasonic probe 2, and the reflection echo signal is subjected to processing such as analog digital conversion. The transmission/reception separating unit 7 transmits the driving signal to be supplied to the ultrasonic probe 2 and the reflection echo signal received from the ultrasonic probe 2 while performing a switching operation between these signals.

The phasing and adding unit 10 subjects the received reflection echo signal to phasing addition. The image processing unit 12 constructs an ultrasonic image (for example, tomogram, blood stream image or the like) on the basis of the phasing-added reflection echo signal. The display unit 14 displays the image-processed ultrasonic image on a display screen. The control unit 16 controls the respective constituent elements described above. The operation unit 18 gives an instruction to the control unit 16, and comprises a track ball, a keyboard or the like. The ultrasonic probe 2 contains a memory 3 in which information concerning the ultrasonic probe (for example, bias voltage, collapse voltage) is stored.

Figure 2:
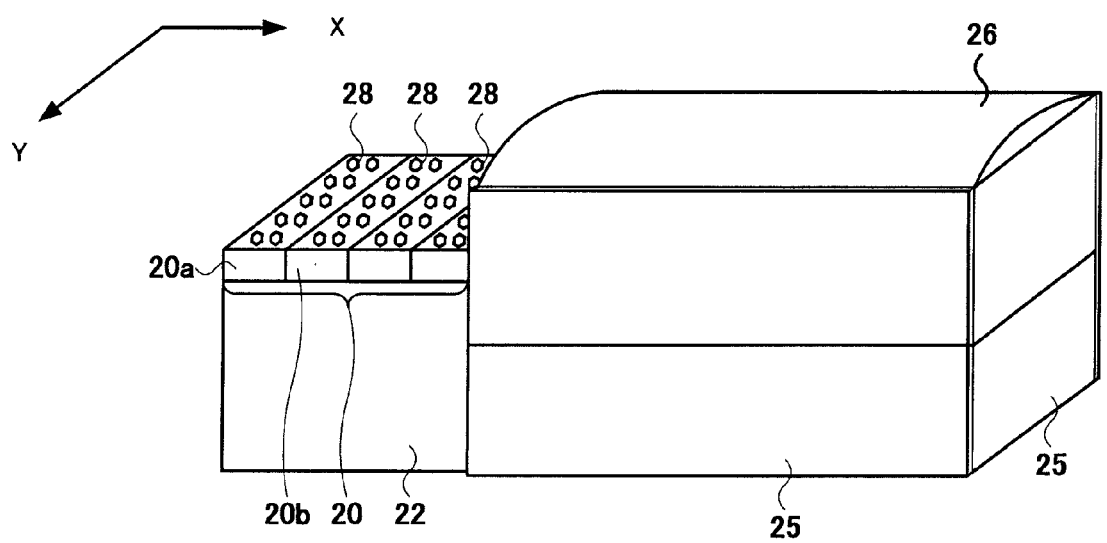
FIG. 2 is a diagram showing the construction of an ultrasonic probe according to the invention.

Next, the ultrasonic probe 2 will be described in detail with reference to FIG. 2. FIG. 2 is a perspective view showing the ultrasonic probe 2. As shown in FIG. 2, the ultrasonic probe 2 is designed as a one-dimensional array type in which plural transducers 20*a* to 20*m* (m: natural number) are arranged in a strip-like shape. However, other types such as a two-dimensional array type and a convex type may be used. A backing layer 22 is provided at the backside of the transducers 20*a* to 20*m*, and also a matching layer 24 is disposed at the ultrasonic wave emission side. An acoustic lens 26 is provided at the ultrasonic emission side of the matching layer 24. The matching layer 24 enhances the transmission efficiency of ultrasonic waves by matching the acoustic impedance between the transducers 20*a* to 20*m* and the examinee. A construction that the matching layer 24 is not used may be adopted.

The transducers 20*a* to 20*m* convert the driving signal from the transmission unit 4 and the bias voltage supply unit 6 to an ultrasonic wave, and transmit the ultrasonic wave to the examinee. The transducers 20*a* to 20*m* convert the ultrasonic wave generated from the examinee to an electrical signal, and receive the ultrasonic wave as a reflection echo signal. The backing layer 22 absorbs propagation of the ultrasonic wave emitted from the transducers 20*a* to 20*m* to the backside thereof, and suppresses extract vibration. The acoustic lens 26 converges the ultrasonic wave transmitted from the transducers 20*a* to 20*m*, and the curvature thereof is determined on the basis of one focal distance.

Figure 3:
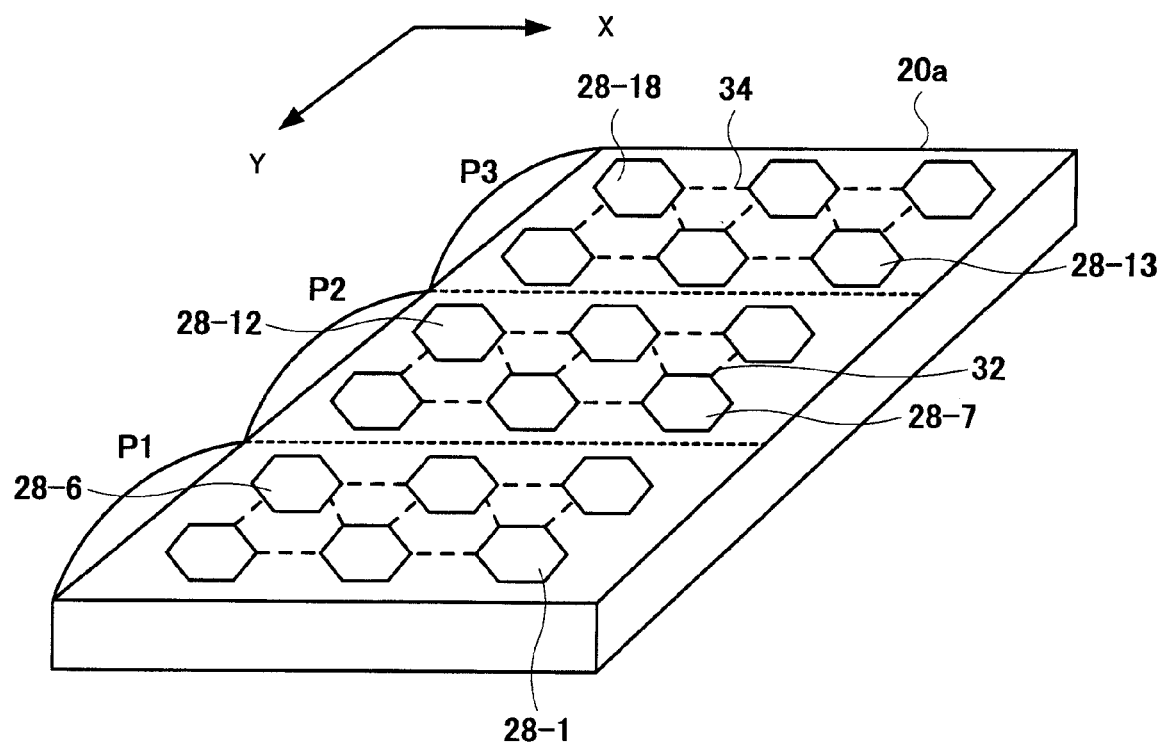
FIG. 3 is a diagram showing the construction of a transducer according to the invention.

Here, the transducers 20*a* to 20*m* and the vibrating element 28 will be described in detail. FIG. 3 is a perspective view showing the transducers 20*a* to 20*m*. As shown in FIG. 3, the transducer 20*a* is divided into plural equal electrical patterns in the minor-axis direction (Y) of the ultrasonic probe 2, for example, three sections P1 to P3. In the section P1, plural, for example, six vibrating elements 28-1 to 28-6 are arranged. A driving electrode is commonly connected to the respective vibrating elements 28-1 to 28-6. Likewise, a driving electrode is commonly connected to the vibrating elements 28-7 to 28-12 belonging to the section P2. A driving electrode is commonly connected to the vibrating elements 28-13 to 28-18 arranged in the section P3.

The vibrating elements 28-1 to 28-18 as described above are electro-acoustic transducers for changing the electromechanical coupling coefficient, that is, the transmission/reception sensitivity in accordance with the magnitude of a bias voltage which is applied thereto by the bias voltage supply unit 6, converting the driving signal supplied from the transmission unit 4 to the ultrasonic wave on the basis of the electromechanical coupling coefficient, transmitting the converted ultrasonic wave, and converting a received ultrasonic wave to an electrical signal to receive the ultrasonic wave as a reflection echo signal.

Figure 4:
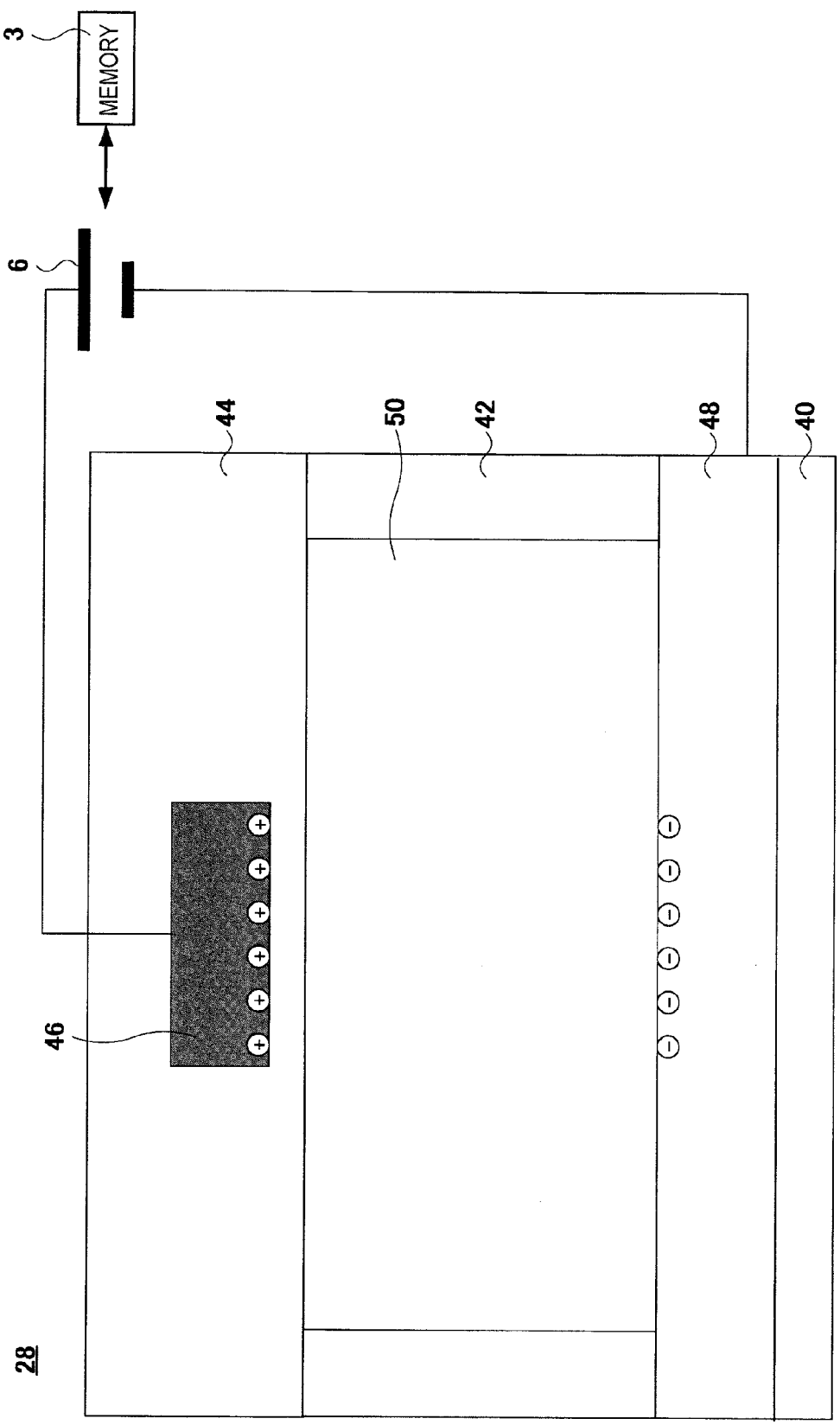
FIG. 4 is a diagram showing the construction of an vibrating element according to the invention.

FIG. 4 is a diagram showing the structure of the vibrating element 28. The vibrating element 28 is formed by microfabrication in the semiconductor process, and it comprises a semiconductor substrate 40, a frame body 42, a film body 44, an upper electrode 46, a lower electrode 48, etc. The frame body 42 is formed of semiconductor compound (for example, insulator such as oxide film (PTEOS) or silicon nitride (SIN)), and it is mounted on the surface at the ultrasonic wave emission side of the lower electrode 48 on the semiconductor substrate 40. The film body 44 is formed of semiconductor compound (for example, insulator such as oxide film (PTEOS) or silicon nitride (SIN)), and it is mounted on the surface at the ultrasonic wave emission side of the frame body 42. Furthermore, the upper electrode 46 is provided to the film body 44. The upper electrode 46 and the lower electrode 48 are connected to the transmission unit 4 containing a power source for supplying a driving signal, and the bias voltage supply unit 6 for applying a DC bias voltage (electric field intensity). A gap 50 as an internal space compartmented by the frame body 42 and the film body 44 is kept to a vacuum state or a state in which predetermined gas is filled. The vibrating element 28 is cMUT (capacitive Micromachined Ultrasonic Transducer: IEEE Trans. Ultrason. Ferroelect. Freq. Contr. Vol 45 pp. 678-690 May 1998).

Figure 5:
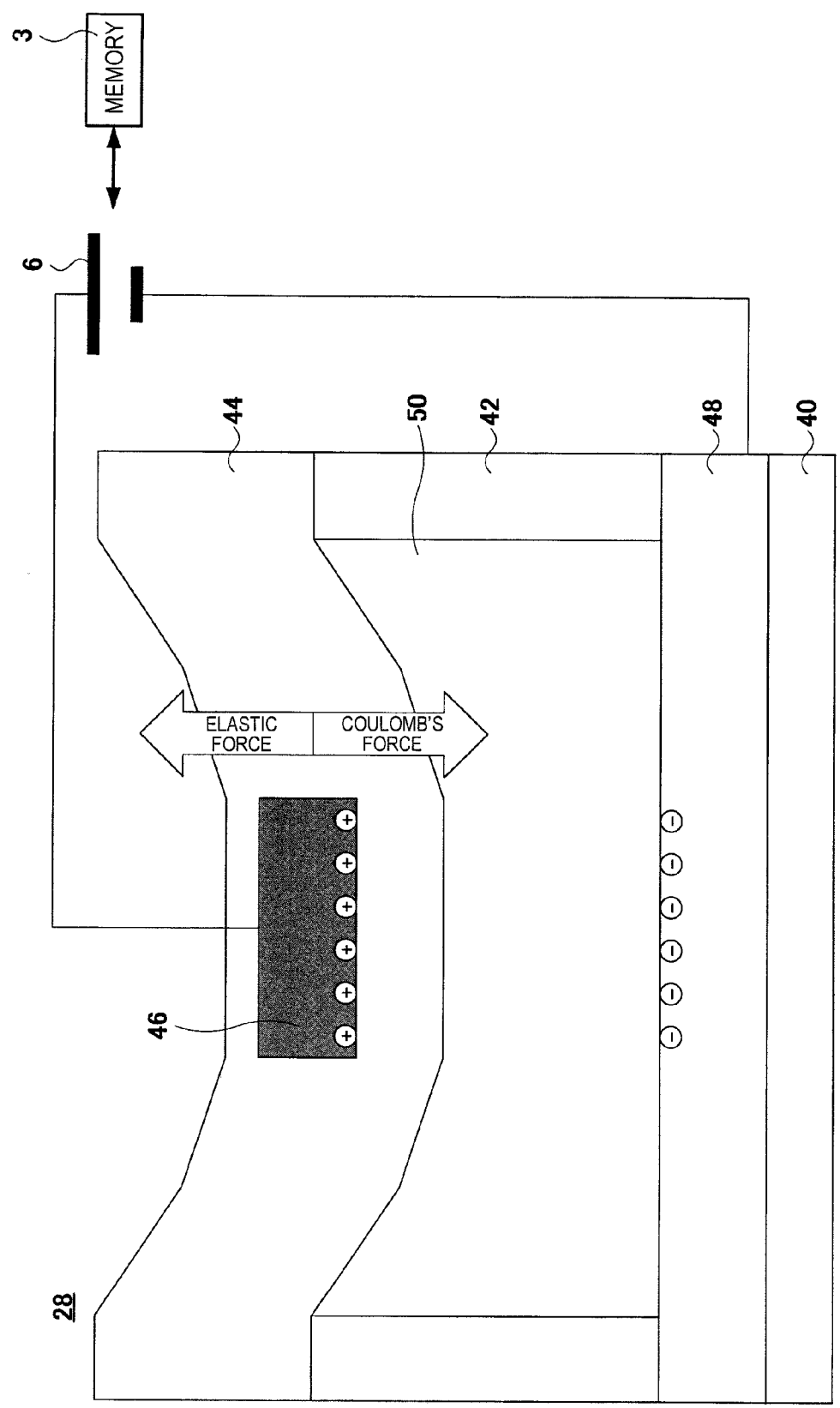
FIG. 5 is a diagram showing a driving state of the vibrating element of the invention.

The operation of the vibrating element 28 will be described with reference to FIG. 5. First, a DC bias voltage (Va) is applied to the vibrating elements 28 through the upper electrode 46 and the lower electrode 48 by the bias voltage supply unit 6. Electric field is generated between the upper electrode 46 and the lower electrode 48 by the bias voltage (Va). The film body 44 is strained by the generated electric field, whereby the electromechanical coupling coefficient is equal to $k_t^2a$. Under this state, the elastic force caused by the film body 44 and the Coulomb's force caused by the bias voltage are balanced with each other. By supplying the driving signal from the transmission unit 4 to the film body 44, the film body 44 is vibrated on the basis of the electromechanical coupling coefficient ($k_t^2a$), and an ultrasonic wave is emitted from the film body 44.

Furthermore, in place of the bias voltage (Va), a bias voltage (Vb) is applied to the vibrating elements 28. In this case, the electromechanical coupling coefficient ($k_t^2b$). Then, the driving signal is supplied from the transmission unit 4 to the film body 44, whereby an ultrasonic wave is emitted from the film body 44 on the basis of the electromechanical coupling coefficient ($k_t^2b$). For Va<Vb, $k_t^2a<k_t^2b$ is satisfied. When an ultrasonic wave is received, the vibration of the film body 44 is likewise excited by a reflection echo signal generated from the examinee, whereby the capacitance of the internal space 48 varies and an electrical signal is obtained on the basis of the variation amount of the varying internal space 48.

That is, the electromechanical coupling coefficient of the vibrating elements 28 is determined on the basis of the tension of the film body 44. Accordingly, the tension of the film body 44 is controlled by varying the magnitude of the bias voltage applied to the vibrating elements 28, whereby the sound pressure (for example, amplitude) of the ultrasonic wave emitted from the vibrating elements 28 can be varied even when a driving signal having the same amplitude is input.

Figure 6:
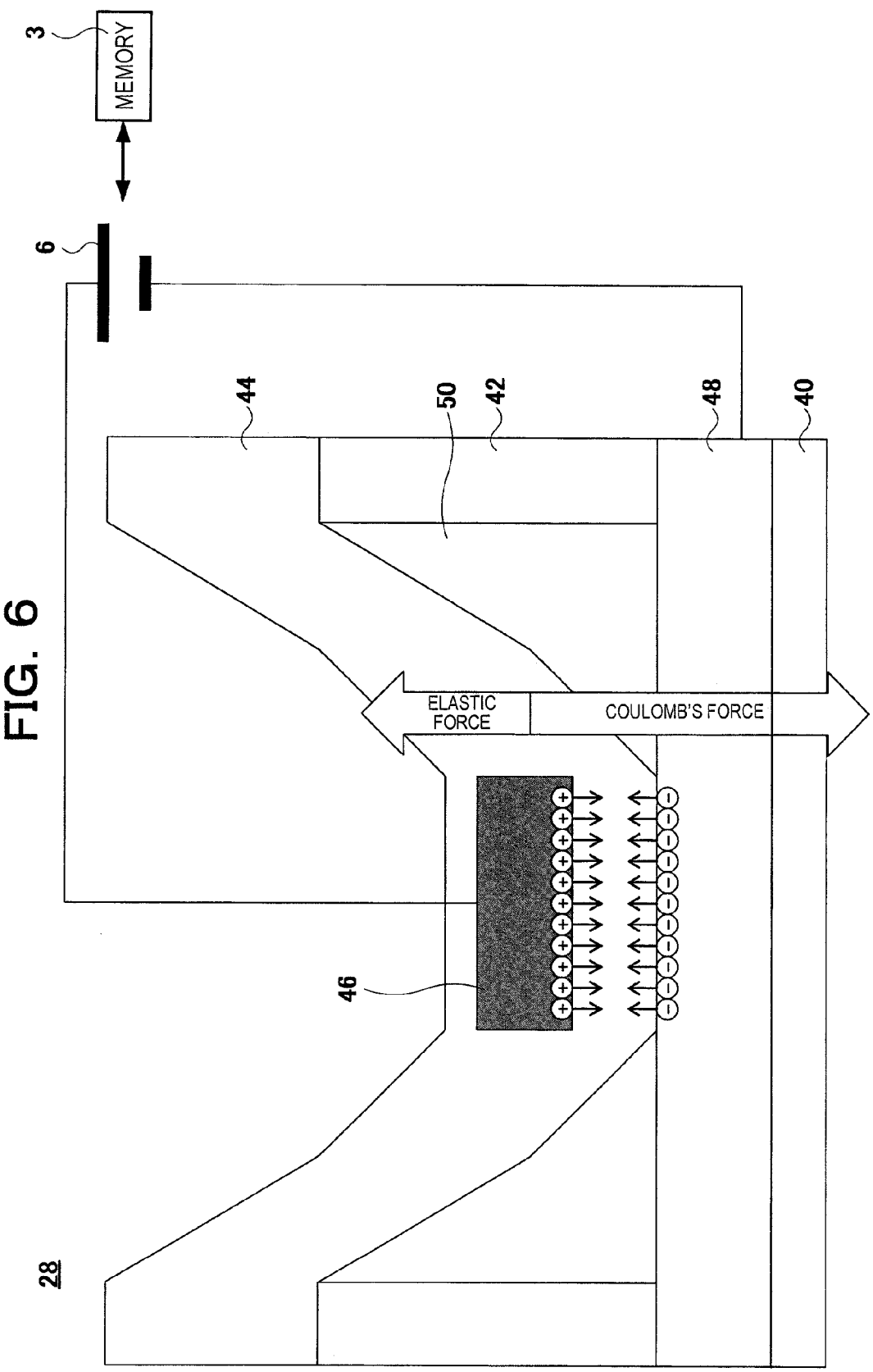
FIG. 6 is a diagram showing a collapse state of the vibrating element of the invention.

When the bias voltage applied to the vibrating elements 28 is increased by the bias voltage supply unit 6, the Coulomb's force based on the bias voltage exceeds the elastic force of the film body 44. Then, as shown in FIG. 6, the center portion of the film body 44 is gradually greatly deformed as the bias voltage increases. Furthermore, when the bias voltage exceeds a value called collapse voltage, the center portion of the film body 44 (containing the upper electrode 46) comes into contact with the surface of the lower electrode 48 on the semiconductor substrate 40. This state corresponds to a collapse state. When the collapse state continues for a long time, charges are trapped (moved) to the film body 44 (insulator) between the lower electrode 48 and the upper electrode 46 although the amount of the moved charges is slight. Subsequently, when the bias voltage is applied to the vibrating elements 28, the electric field decreases to a smaller value than that before the collapse state because of the trapped charges to the film body 44 between the lower electrode 48 and the upper electrode 46, so that the electromechanical coupling coefficient decreases and thus the sound pressure of the ultrasonic wave emitted from the vibrating elements 28 also decreases.

Therefore, it is important that the collapse voltage is measured in advance and the bias voltage being used is set to be equal to or less than the collapse voltage.

Here, a first embodiment will be described with reference to FIGS. 1 to 8. The collapse voltage of the vibrating elements 28 of the ultrasonic probe 2 is measured in advance, the bias voltage is calculated from the measured collapse voltage and the calculated bias voltage is stored in the memory 3 of the ultrasonic probe 2. The bias voltage is a voltage lower than the collapse voltage. When an ultrasonic wave is transmitted/received, the bias voltage is output from the memory 3 to the bias voltage supply unit 6, and the bias voltage supply unit 6 sets the bias voltage.

The first embodiment will be specifically described. The collapse voltage of one certain vibrating element 28 in the transducers 20*a* to 20*m* is measured. For example, a vibrating element 28 which is set at the end portion of the transducers 20*a* to 20*m* is suitably used as the vibrating element 28 whose collapse voltage is to be measured because this vibrating element 28 hardly affects the transmission/reception of ultrasonic waves. In this embodiment, it is assumed that the vibrating elements 28 of the transducers 20*a* to 20*m* are substantially uniformly constructed.

Figure 7:
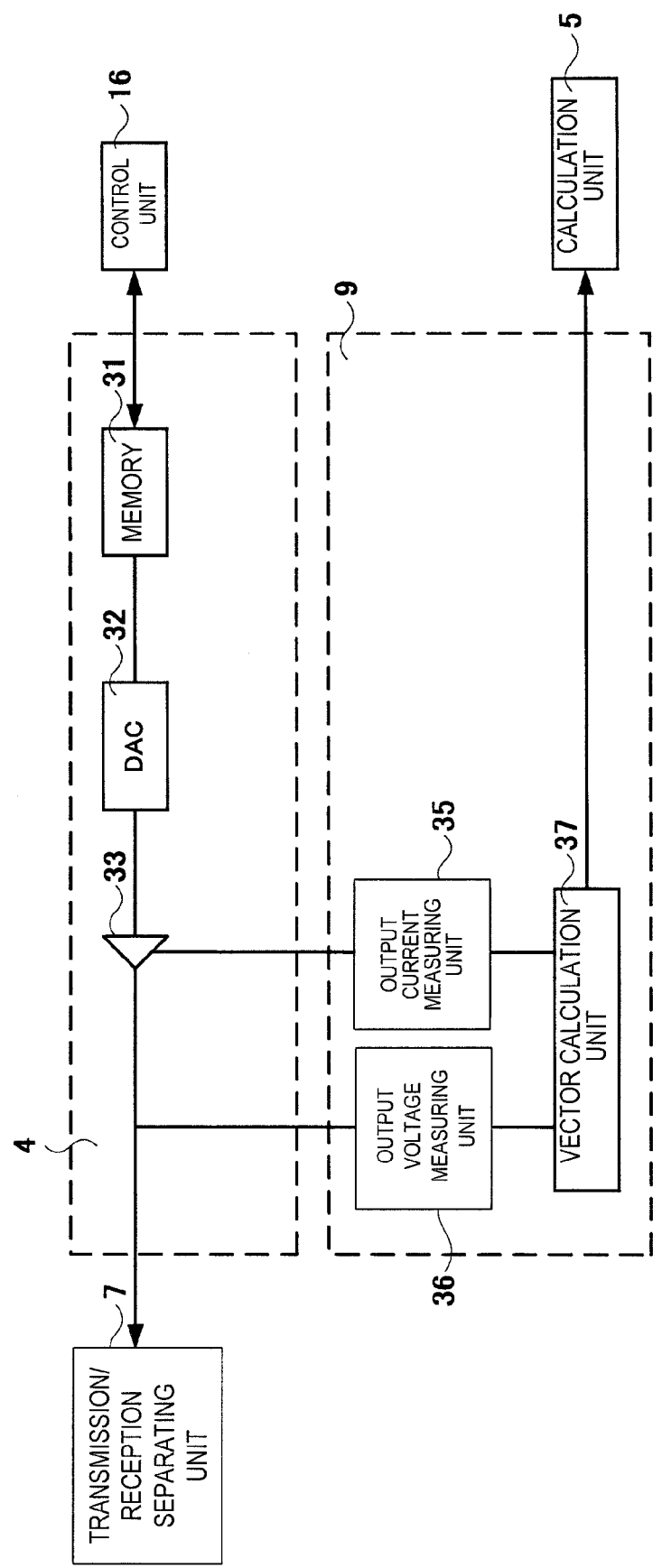
FIG. 7 is a diagram showing the details of a capacitance measuring unit and a transmission unit according to the invention.

As shown in FIG. 7, the transmission unit 4 comprises a memory 31 in which various kinds of transmission waveform data are stored, a digital analog converter (hereinafter referred to as DAC) 32 which is connected to the memory 31 and converts transmission waveform data read out from the memory 31 to an analog signal, and a pulser 33 that is connected to DAC 32, amplifies the analog signal and generates a transmission waveform for emitting an ultrasonic wave from the vibrating elements 28. The memory 31 is connected to the control unit 16.

The capacitance measuring unit 9 for measuring the capacitance value of the vibrating elements 28 comprises an output current measuring unit 35 for measuring output current, an output voltage measuring unit 36 for measuring an output voltage, and a vector calculation unit 37. The output current measuring unit 35 is disposed between the output of the pulser 33 and the vibrating elements 28 (not shown), and measures the output current of the transmission waveform. The output voltage measuring unit 36 is disposed between the pulser 33 and the reference potential of GND (not shown), and measures the voltage of the transmission waveform. The respective outputs of the output current measuring unit 35 and the output voltage measuring unit 36 are connected to the vector calculation unit 37, and impedance and reactance are determined on the basis of the intensities of the voltage and the current, and the phase relationship between the voltage and the current. The vector calculation unit 37 determines the capacitance value of the vibrating elements 28 from the reactance component by calculation. The capacitance measuring unit 9 can be shared with the circuit of the transmission unit 4.

The pulser 33 outputs a sin waveform signal of a low frequency (10 k to 1 MHz) to the vibrating elements 28. The bias voltage supply unit 6 applies the bias voltage between the upper electrode 46 and the lower electrode 48 of the vibrating elements 28 while varying the bias voltage. In the vibrating elements 28, the electric field intensity, that is, the Coulomb's force between the upper electrode 46 and the lower electrode 48 varies in accordance with the variation of the bias voltage, and the gap 50 varies due to the balance between the Coulomb's force and the elastic force based on the film body 44. At this time, the vector calculation unit 37 calculates the capacitance value by using the current waveform and the voltage waveform detected by the output current measuring unit 35 and the output voltage measuring unit 36. The current I(t) is under the state that the phase thereof advances by substantially 90° as compared with the sin voltage V(t) of the low frequency, and thus the reactance component is under the state that it substantially indicates the capacitance value. Accordingly, the vector calculation unit determines the capacitance value on the basis of the reactance component by calculation.

Figure 8:
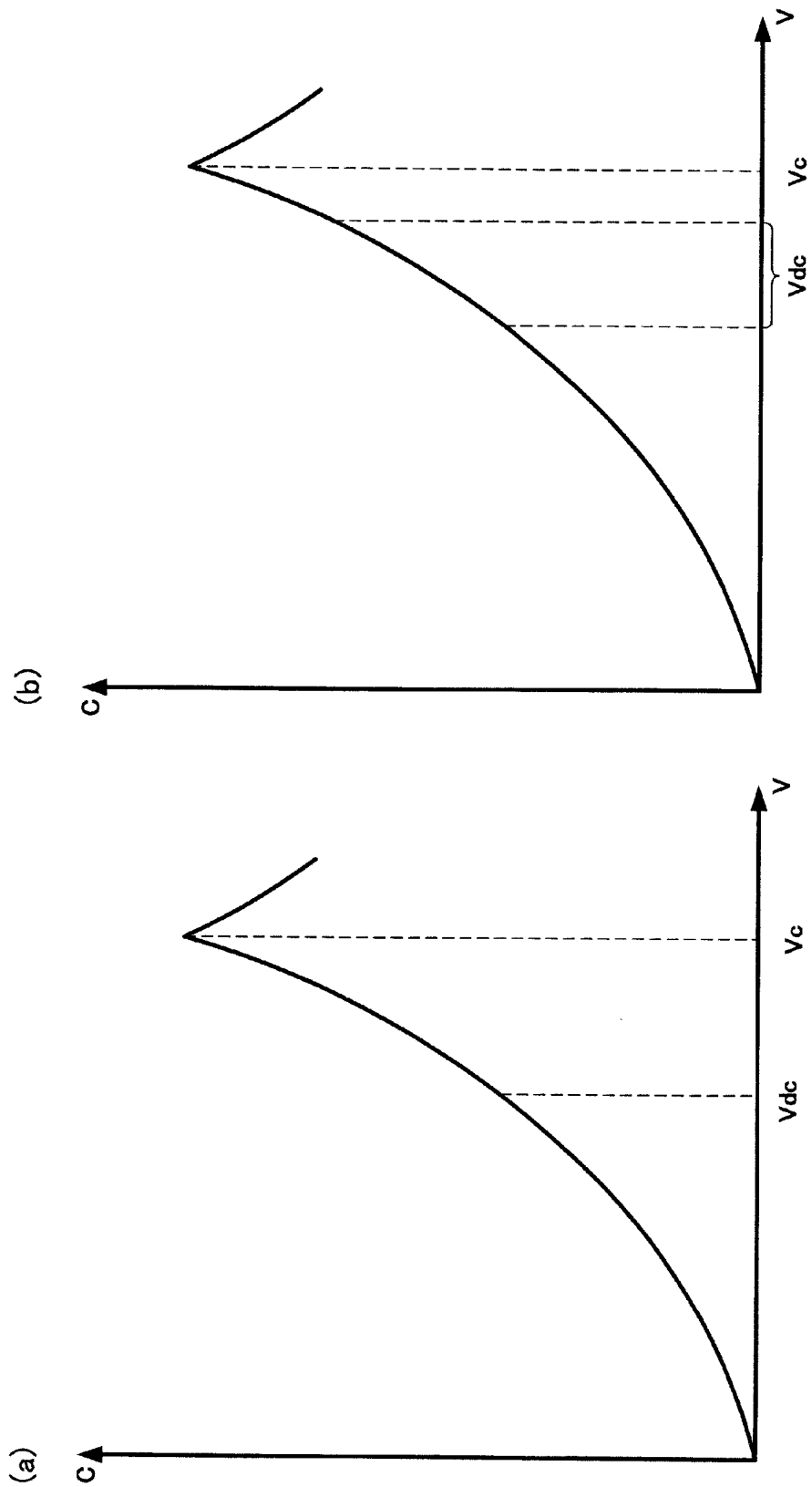
FIG. 8 is a diagram showing a first embodiment and a second embodiment of the invention.

The calculation unit 5 traces the relationship between the bias voltage applied to the vibrating elements 28 by the bias voltage supply unit 6 and the capacitance value determined by the capacitance measuring unit 9, thereby extracting a CV curve. When the applied voltage of the bias voltage supply unit 6 is gradually increased from a small value, the capacitance value increases in accordance with the increase of the bias voltage. As shown in FIG. 8, the collapse voltage (Vc) of the vibrating elements 28 is represented by a point at which the increase of the capacitance value is stopped on the CV curve.

The calculation unit 5 differentiates the waveform of the extracted CV curve. The calculation unit 5 measures as the collapse voltage (Vc) a point at which the gradient (derivative value) varies from positive to negative. The collapse voltage (Vc) is a bias voltage under the state that the center portion of the film body 44 comes into contact with the surface of the lower electrode 48 on the semiconductor substrate 40.

As shown in FIG. 8(a), the calculation unit 5 calculates as the bias voltage (Vdc) a voltage which is lower than the collapse voltage (Vc), for example, equal to 70% of the collapse voltage (Vc). The calculation unit 5 stores the calculated bias voltage (Vdc) into the memory 3.

When the ultrasonic wave is transmitted/received, the bias voltage (Vdc) is read out from the memory 3, and the bias voltage (Vdc) of he bias voltage supply unit 6 is set. The bias voltage supply unit 6 applies the bias voltage (Vdc) to the respective vibrating elements 28 of the transducers 20a to 20m. That is, the same bias voltage (Vdc) is applied to the vibrating elements 28 of all the channels. The driving signal is supplied from the transmission unit 4 to the film body 44, whereby the ultrasonic wave is emitted from the film body 44 on the basis of the electromechanical coupling coefficient based on the bias voltage (Vdc).

In this embodiment, the voltage of 70% of the collapse voltage (Vc) is set as the bias voltage (Vdc). Therefore, even when slight dispersion (about ±10%) exists among the collapse voltages (Vc) of the respective vibrating elements 28 of the transducers 20a to 20m, the respective vibrating elements 28 do not reach the collapse voltage (Vc). The bias voltage supply unit 6 can set a bias voltage which is equal to or less than the bias voltage (Vdc).

As described above, according to this embodiment, the bias voltage set by the bias voltage supply unit 6 does not reach the collapse voltage, and thus the center portion of the film body 44 does not come into contact with the surface of the lower electrode 48 on the semiconductor substrate 40. Accordingly, the movement of charges from the lower electrode 48 to the upper electrode 46 does not occur. Therefore, the sensitivity of the ultrasonic probe 2 can be kept.

In this embodiment, the calculation unit 5 calculates the value of 70% of the collapse voltage (Vc) as the bias voltage (Vdc), however, this embodiment is not limited to this value. As shown in FIG. 8(b), the operation unit 18 can determine what percentages of the collapse voltage (Vc) in a predetermined range should be set as the bias voltage (Vdc). The operation unit 18 can set the calculation unit 5 so that the value in the range from 70% to 90% of the collapse voltage (Vc), for example, 80%, 85%, 90% is set as the bias voltage (Vdc).

Here, a second embodiment will be described. It is different from the first embodiment in that the collapse voltage is stored in the memory 3.

The collapse voltage of the vibrating elements 28 of the ultrasonic probe 2 is measured in advance, and the collapse voltage is stored in the memory 3 of the ultrasonic probe 2. When an ultrasonic wave is transmitted/received, the collapse voltage is output from the memory 3, the calculation unit 5 calculates a bias voltage which is equal to or less than the output collapse voltage, and the bias voltage supply unit 6 sets the bias voltage.

The collapse voltage (Vc) of one vibrating element 28 in the transducers 20a to 20m is measured by the calculation unit 5. This measuring method is the same as the first embodiment, and thus the description thereof is omitted. The memory 3 stores the collapse voltage (Vc) of the vibrating element 28 extracted by the bias voltage supply unit 6 and the calculation unit 5.

When the ultrasonic wave is transmitted/received, the calculation unit 5 calculates the bias voltage (Vdc) from the collapse voltage (Vc) information stored in the memory 3. As shown in FIG. 8(a), the calculation unit 5 calculates as the bias voltage (Vdc) a value which is equal to or less than the collapse voltage (Vc), for example, 70% of the collapse voltage (Vc).

The bias voltage supply unit 6 applies the bias voltage (Vdc) to the respective vibrating elements 28 of the transducers 20a to 20m. The driving signal is supplied from the transmission unit 4 to the film body 44, whereby the ultrasonic wave is emitted from the film body 44 on the basis of the electromechanical coupling coefficient based on the bias voltage (Vdc).

According to this embodiment, the bias voltage set by the bias voltage supply unit 6 does not reach the collapse voltage, and thus the center portion of the film body 44 does not come into contact with the surface of the lower electrode 48 on the semiconductor substrate 40. Accordingly, there occurs no movement of charges to the film body 44 between the lower electrode 48 and the upper electrode 46. Therefore, the sensitivity of the ultrasonic probe 2 can be kept.

Here, a third embodiment will be described with reference to FIG. 9. This embodiment is different from the first embodiment and the second embodiment in that collapse voltages are determined from plural vibrating elements 28 and the bias voltage of the bias voltage supply unit 6 is set on the basis of the plural collapse voltages.

Figure 9:
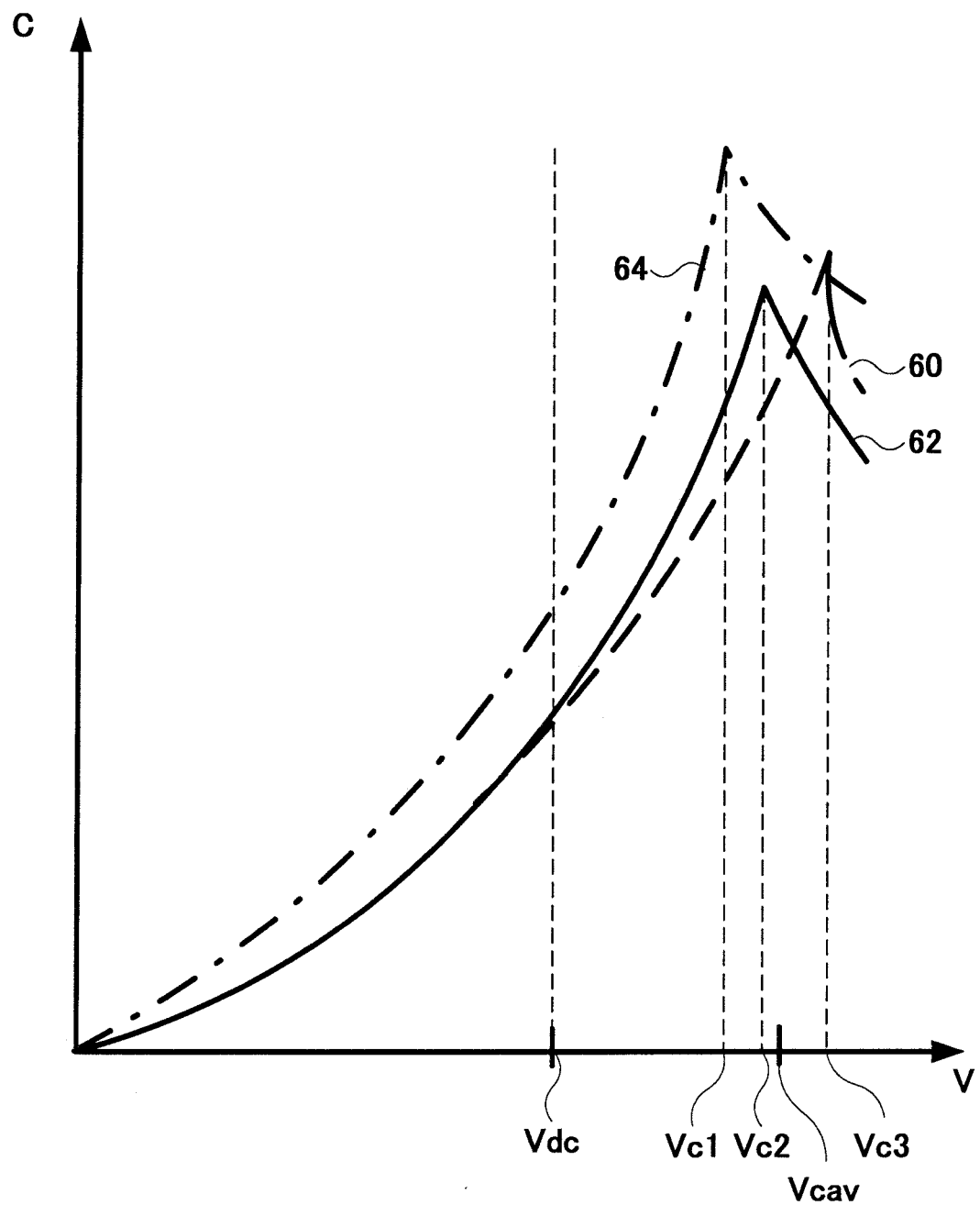
FIG. 9 is a diagram showing a third embodiment of the invention.

As shown in FIG. 9, CV curves are extracted for three vibrating elements 28 in the transducers 20a to 20m, for example. With respect to the first vibrating element, a characteristic as indicated by a broken line 60 is obtained. With respect to the second vibrating element, a characteristic as indicated by a solid line 62 is obtained. With respect to a third vibrating element, a characteristic as indicated by a one-dotted chain line 64 is obtained.

The calculation unit 6 determines collapse voltages (Vc1, Vc2, Vc3) in the respective vibrating elements 28. This measuring method is the same as the first embodiment, and thus the description thereof is omitted. The calculation unit 6 calculates the average value (Vcav) of the collapse voltages (Vc1, Vc2, Vc3) from the information on the collapse voltages (Vc1, Vc2, Vc3). Then, the calculation unit 6 calculates the bias voltage (Vdc) from the average value (Vcav) of the collapse voltages. As shown in FIG. 9, the calculation unit 6 calculates as the bias voltage (Vdc) a value which is equal to or less than the average value (Vcav) of the collapse voltages, for example, a value of 70%. The memory 3 stores the calculated bias voltage.

When the ultrasonic wave is transmitted/received, the bias voltage (Vdc) is read out from the memory 3, and the bias voltage (Vdc) of the bias voltage supply unit 6 is set. The bias voltage supply unit 6 applies the bias voltage (Vdc) to the respective vibrating elements 28 of the transducers 20a to 20m. Then, the driving signal is supplied from the transmission unit 4 to the film body 44, whereby the ultrasonic wave is emitted from the film body 44 on the basis of the electromechanical coupling coefficient based on the bias voltage (Vdc).

In this embodiment, a value which is not more than the average value (Vcav) of the collapse voltages in the plural vibrating elements 28, that is, the value of 70% is set as the bias voltage (Vdc). Accordingly, this embodiment is effective even when the collapse voltage (Vc) is slightly dispersed among the plural vibrating elements 28.

Furthermore, the calculation unit 6 determines the average value (Vcav) of the collapse voltage from the collapse voltages (Vc1, Vc2, Vc3) of these vibrating elements 28. However, the bias voltage (Vdc) may be calculated on the basis of the minimum value (Vc1) of the collapse voltage. For example, the calculation unit 6 calculates as the bias voltage (Vdc) a value which is not more than the minimum value (Vc1) of the collapse voltage, for example, a value of 70%. Accordingly, the bias voltage can be set in the bias voltage supply unit 6 with preventing the bias voltage of each of the vibrating elements 28 from reaching the collapse voltage.

According to this embodiment, the bias voltage set by the bias voltage supply unit 6 does not reach the collapse voltage. Therefore, the center portion of the film body 44 does not come into contact with the surface of the lower electrode 48 on the semiconductor substrate 40. Accordingly, movement of charges to the film body 44 between the lower electrode 48 and the upper electrode 46 does not occur, so that the sensitivity of the ultrasonic probe 2 can be kept.

In this embodiment, the collapse voltages (Vc1, Vc2, Vc3) of the three vibrating elements 28 in the transducers 20a to 20m are extracted to determine the bias voltage (Vdc). However, this embodiment is not limited to the three vibrating elements 28. For example, the collapse voltages (Vc1 to Vc5) of five vibrating elements 28 in the transducers 20a to 20m may be extracted to determine the bias voltage (Vdc). Furthermore, the collapse voltage of one vibrating element 28 may be extracted every transducer 20a to 20m to determine bias voltage (Vdc). The above choice may be arbitrarily made by the operation unit 18. Furthermore, in this embodiment, the bias voltage (Vdc) is extracted on the basis of the average value of the collapse voltages, but the bias voltage (Vdc) may be extracted on the basis of another definition such as the median value of the collapse voltages or the minimum value of the collapse voltages.

Figure 10:
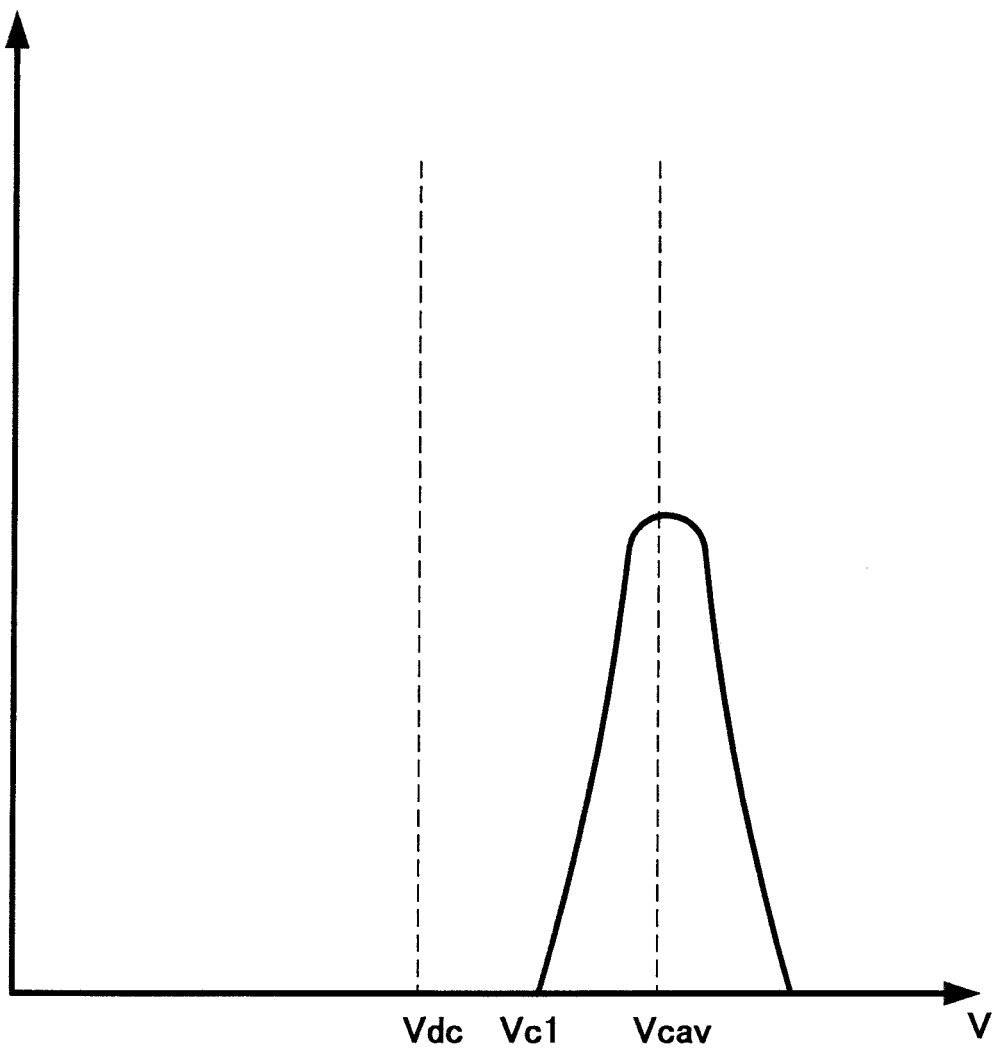
FIG. 10 is a diagram showing a fourth embodiment of the invention.

Here, a fourth embodiment will be described with reference to FIG. 10. This embodiment is different from the first to third embodiments in that the collapse voltages of all the vibrating elements 28 are determined and the bias voltage of the bias voltage supply unit 6 is set on the basis of all the collapse voltages.

First, CV curves are extracted for all the vibrating elements 28 of the transducers 20a to 20m by the calculation unit 5. The calculation unit 6 determines the collapse voltage of each of the vibrating elements 28. This measuring method is the same as the first embodiment, and thus the description thereof is omitted.

The calculation unit 6 determines a histogram representing frequency/number of times of the collapse voltages (Vc). Then, the calculation unit 6 determines the average value and the median value (Vca) in the determined histogram. Furthermore, the calculation unit 6 calculates the bias voltage (Vdc) from the average value or the median value (Vcav) of the collapse voltages (Vc). As shown in FIG. 10, the calculation unit 6 calculates as the bias voltage (Vdc) a value which is not more than the average value or median value (Vcav) of the collapse voltages, for example, a value of 70% of the collapse voltage. The memory 3 stores the calculated bias voltage (Vdc).

When the ultrasonic wave is transmitted/received, the bias voltage (Vdc) is read out from the memory 3, and the bias voltage (Vdc) of the bias voltage supply unit 6 is set. The bias voltage supply unit 6 applies the bias voltage (Vdc) to the respective vibrating elements 28 of the transducers 20a to 20m. The driving signal is supplied from the transmission unit 4 to the film body 44, whereby the ultrasonic wave is emitted from the film body 44 on the basis of the electromechanical coupling coefficient based on the bias voltage (Vdc).

Furthermore, the calculation unit 6 determines the average value or median value (Vcav) of the histogram from the collapse voltages (Vc) of all the vibrating elements 28. However, the bias voltage (Vdc) maybe calculated on the basis of the minimum value (Vc1) of the histogram. For example, the calculation unit 6 calculates the bias voltage (Vdc) so that the bias voltage (Vdc) is equal to 70% of the minimum value (Vc1) of the collapse voltages. Accordingly, the bias voltage can be set in the bias voltage supply unit 6 so that the bias voltage does not reach the collapse voltages of the respective vibrating elements 28.

According to this embodiment, the bias voltage set in the bias voltage supply unit 6 does not reach the collapse voltages of all the vibrating elements 28. Therefore, the center portion of the film body 44 does not come into contact with the surface of the lower electrode 48 on the semiconductor substrate 40. Accordingly, the movement of charges to the film body 44 between the lower electrode 48 and the upper electrode does not occur. Therefore, the sensitivity of the ultrasonic probe 2 can be kept.

Here, a fifth embodiment will be described with reference to FIG. 11. This embodiment is different from the first to fourth embodiment in that the collapse voltage is measured with time lapse to update the bias voltage or collapse voltage stored in the memory 3.

First, the bias voltage or the collapse voltage is stored in the memory 3 as in the case of the first to fourth embodiments. For example, when one month or one year elapses from the time of storage into the memory 3, the collapse voltage(s) of one vibrating element 28, plural vibrating elements 28 or all the vibrating elements 28 in the transducers 20a to 20m is(are) measured by the bias voltage supply unit 6, the calculation unit 5 and the capacitance measuring unit 9. In this case, the collapse voltage(s) is(are) measured when one month or one year elapses, however, the time period may be arbitrarily set by the operation unit 18.

Figure 11:
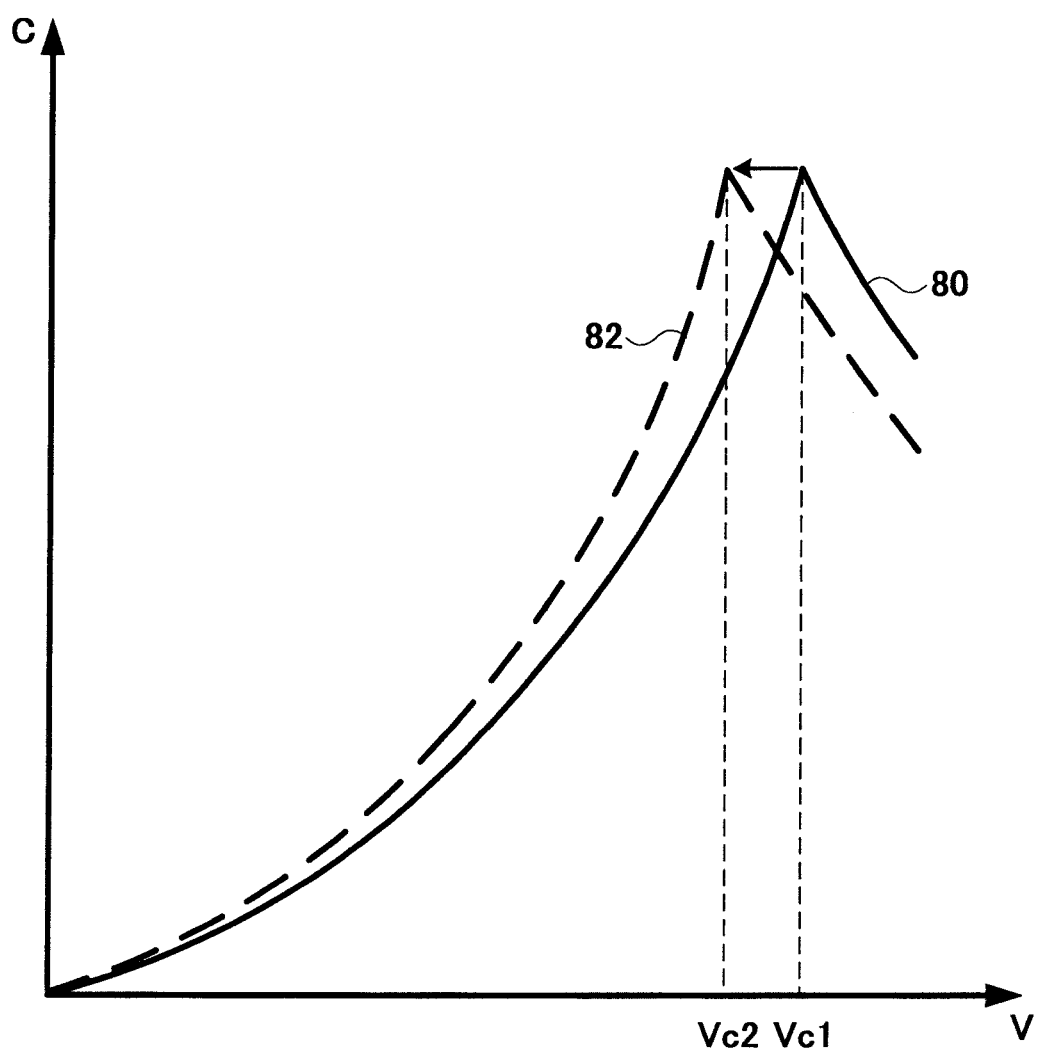
FIG. 11 is a diagram showing a fifth embodiment of the invention.

As shown in FIG. 11, the collapse voltage (Vc) of the vibrating element 28 is represented by a point at which the increase of the capacitance stops in the CV curve. A solid-line CV curve 80 represents past actual measurement values, and a broken-line CV curve 82 represents present actual measurement value.

The calculation unit 6 calculates a bias voltage (Vdc1) which is not more than the collapse voltage (Vc1) extracted from the actual-line CV curve 80. The calculated bias voltage (Vdc1) is stored in the memory 3. The calculation unit 6 calculates a bias voltage (Vdc2) which is not more than the collapse voltage (Vc2) extracted from the broken-line CV curve 82. The memory 3 stores the calculated bias voltage (Vdc2) while replacing the bias voltage (Vdc1) by the calculated bias voltage (Vdc2).

When the ultrasonic wave is transmitted/received, the bias voltage (Vdc2) is read out from the memory 3, and the bias voltage (Vdc2) of the bias voltage supply unit 6 is set. The bias voltage supply unit 6 applies the bias voltage (Vdc2) concerned to the respective vibrating elements 28 of the transducers 20a to 20m. Then, the driving signal is supplied from the transmission unit 4 to the film body 44, whereby the ultrasonic wave is emitted from the film body 44 on the basis of the electromechanical coupling coefficient based on the bias voltage (Vdc2).

According to this embodiment, the bias voltage is set in accordance with the variation of the collapse voltage which is caused by the time deterioration of the vibrating elements 28, and thus the bias voltage does not reach the collapse voltage. The center portion of the film body 44 does not come into contact with the surface of the lower electrode 48 on the semiconductor substrate 40, and thus movement of charges to the film body 44 between the lower electrode 48 and the upper electrode 46 does not occur. Therefore, the sensitivity of the ultrasonic probe 2 can be kept.

In this embodiment, the collapse voltage is measured at the time when one month or one year elapses and the bias voltage is updated. However, the collapse voltage may be measured at a rate of once per 500 times of diagnosis to update the bias voltage in the memory 3, for example.

Here, a sixth embodiment will be described. This embodiment is different from the first to fifth embodiments in that the bias voltage corresponding to the type of the vibrating elements 28 is set.

When the diameter of the vibrating element 28 is large, the rigidity of the film body 44 is small and thus the collapse voltage (Vc) is low. On the other hand, when the diameter of the vibrating element 28 is small, the rigidity of the film body 44 is large and thus the collapse voltage (Vc) increases. Furthermore, when the gap 50 between the vibrating elements 28 is large, the electric field intensity is small and thus the collapse voltage (Vc) is high. On the other hand, when the gap 50 of the vibrating element 28 is small, the electric field intensity is high and thus the collapse voltage (Vc) is low. Furthermore, the collapse voltage also varies in accordance with the dielectric constant of the film body 44 or the like. Because of the characteristic as described above, it is necessary to settle the collapse voltage (Vc) in accordance with the structure or type of the vibrating elements 28 and set the bias voltage.

Therefore, in this embodiment, the collapse voltage (Vc) is measured in accordance with the type of the vibrating elements 28 (for example, the gap or diameter) mounted on the ultrasonic probe 2. This measuring method is the same as the first embodiment, and thus the description thereof is omitted. The calculation unit 5 calculates as the bias voltage (Vdc) a voltage which is not more than the collapse voltage (Vc) measured in accordance with the type of the vibrating elements 28, for example, a voltage of 70% of the collapse voltage (Vc). The calculation unit 5 stores the calculated bias voltage into the memory 3 together with information about the type of the vibrating elements 28.

When the ultrasonic wave is transmitted/received, the bias voltage (Vdc) corresponding to the type of the vibrating elements 28 is read out from the memory 3, and the bias voltage (Vdc) of the bias voltage supply unit 6 is set. The bias voltage supply unit 6 associates the bias voltage (Vdc) and the type of the vibrating elements 28 with each other, and applies the bias voltage (Vdc) to the respective vibrating elements 28. Then, the driving signal is transmitted from the transmission unit 4 to the film body 44, whereby the ultrasonic wave is emitted from the film body 44 on the basis of the electromechanical coupling coefficient based on the bias voltage (Vdc).

According to this embodiment, the bias voltage is set in accordance with the change of the collapse voltage which is made in accordance with the type of the vibrating elements 28, and thus the bias voltage does not reach the collapse voltage. The center portion of the film body 44 does not come into contact with the surface of the lower electrode 48 on the semiconductor substrate 40, and thus the movement of charges to the film body 44 between the lower electrode 48 and the upper electrode 46 does not occur. Therefore, the sensitivity of the ultrasonic probe 2 can be kept.

Figure 12:
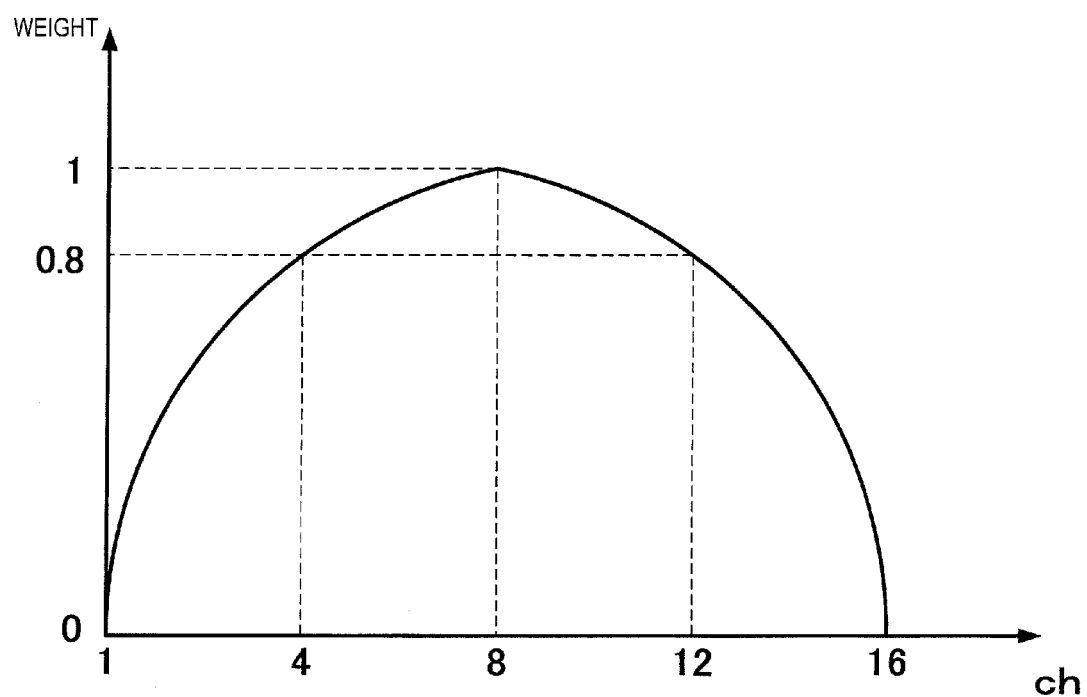
FIG. 12 is a diagram showing a seventh embodiment of the invention.

Here, a seventh embodiment will be described with reference to FIG. 12. This embodiment is different from the first to sixth embodiments in that a weight for the bias voltage is set every channel.

The bias voltage supply unit 6 sets the bias voltage varying every channel on the basis of the bias voltage (Vdc) determined by the calculation unit 5.

First, the collapse voltage (Vc) of one certain vibrating element 28 in the transducers 20a to 20m is measured. The measuring method is the same as the first embodiment, and thus the description thereof is omitted. The calculation unit 5 calculates as the bias voltage (Vdc) a voltage which is not more than the collapse voltage (Vc), for example, a voltage of 70% of the collapse voltage (Vc). The memory 3 stores the bias voltage (Vdc).

The bias voltage supply unit 6 increases the weight for the bias voltage (Vdc) of the channel at the center portion of the ultrasonic probe 2, and reduces the weight for the bias voltage (Vdc) of the channel at the end portion. Specifically, as shown in FIG. 12, the bias voltage supply unit 6 sets "1" to the weight for the bias voltage applied to the vibrating elements 28 of an 8-channel. The bias voltage supply unit 6 sets "0.8" to the weight for the bias voltage applied to the vibrating elements 28 of the 4-channel and the 12-channel. The bias voltage supply unit 6 sets "0" to the weight for the bias voltage applied to the vibrating elements 28 of the 1-channel and the 16-channel.

The weight for the bias voltage (Vdc) applied to the 8-channel is largest. With respect to the channels other than the 8-channel, bias voltages which are not more than the bias voltage (Vdc) applied to the 8-channel are set. Accordingly, the bias voltage can be set with preventing the bias voltages of the vibrating elements 28 from reaching the collapse voltages in all the channels. The center portion of the film body 44 does not come into contact with the surface of the lower electrode 48 on the semiconductor substrate 40, and movement of charges to the film body 44 between the lower electrode 48 and the upper electrode 46 does not occur. Therefore, the sensitivity of the ultrasonic probe 2 can be kept.

Furthermore, the bias voltage supply unit 6 can change the distribution of the weights in accordance with the aperture. For example, when the ultrasonic waved is required to be transmitted/received with the aperture containing the 5-channel to the 11-channel, the weights for the 1-channel to the 4-channel and the 12-channel to the 16-channel are set to zero. That is, the bias voltage supply unit 6 sets to "0" the weight for the channels which are not used for the transmission/reception of ultrasonic waves.

Figure 13:
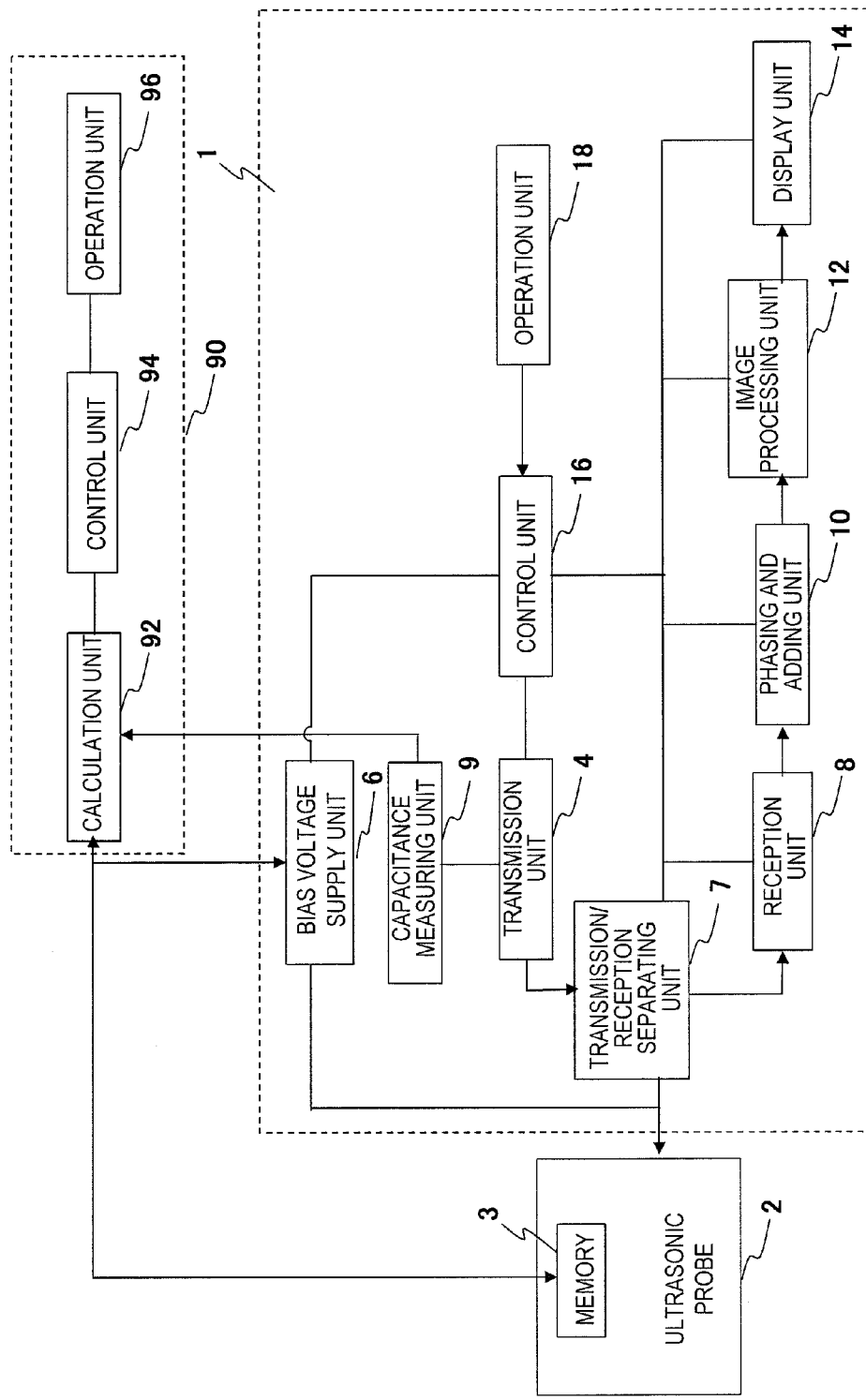
FIG. 13 is a diagram showing an eighth embodiment of the invention.

Here, an eighth embodiment will be described with reference to FIG. 13. This embodiment is different from the first to seventh embodiments in that a calculating device 90 containing a calculation unit 92 for calculating the collapse voltage (Vc) and the bias voltage (Vdc) is provided at the outside of the ultrasonic diagnosis apparatus 1. The duplicative description of the first embodiment will be omitted.

The calculating device 90 comprises the calculation unit 92 for calculating the collapse voltage (Vc) and the bias voltage (Vdc), and a control unit 94 and an operation unit 96 for operating the calculation unit 92.

The calculation unit 92 traces the relationship between the bias voltage applied to the vibrating elements 28 by the bias voltage supply unit 6 and the capacitance value determined by the capacitance measuring unit 9 to extract a CV curve. The calculation unit 92 measures as the collapse voltage (Vc) a point at which the gradient (derivative value) varies from positive to negative. As shown in FIG. 8(*a*), the calculation unit 92 calculates as the bias voltage (Vdc) a voltage which is not more than the collapse voltage (Vc), for example, a value of 70% of the collapse voltage (Vc). The calculation unit 92 stores the calculated bias voltage (Vdc) into the memory 3.

When the bias voltage (Vdc) is temporarily stored into the memory 3 before shipping of products or the like, the connection between the calculating device 90 (calculation unit 92) and the ultrasonic probe 2, the constituent elements in the ultrasonic diagnosis apparatus 1 is released. At this time, the connection state between the memory 3 and the bias voltage supply unit 6 is kept.

When the ultrasonic wave is transmitted/received, the bias voltage (Vdc) is read out from the memory 3, and the bias voltage (Vdc) of the bias voltage supply unit 6 is set. The bias voltage supply unit 6 applies the bias voltage (Vdc) concerned to the respective vibrating elements 28 of the transducers 20*a* to 20*m*. Then, the driving signal is supplied from the transmission unit 4 to the film body 44, whereby the ultrasonic wave is emitted from the film body 44 on the basis of the electromechanical coupling coefficient based on the bias voltage (Vdc).

As described above, according to this embodiment, the calculating device 90 is provided at the outside of the ultrasonic diagnosis apparatus 1, and the connection between the ultrasonic diagnosis apparatus 1 and the calculating device 90 is released before shipping of products, and an inexpensive ultrasonic diagnosis apparatus 1 can be provided.

This embodiment has been described by using the structure that the insulator between the lower electrode 48 and the upper electrode 46 are provided to the film body 44 side. However, the insulator may be also provided onto the lower electrode 48.

The embodiment of the ultrasonic diagnosis apparatus according to the invention has been described, however, the invention is not limited to this embodiment. It is apparent that persons skilled in the art can attain various modifications or alterations within the scope of the technical idea disclosed in this application, and it is naturally understood that they belong to the technical scope of the invention.

The invention claimed is:

1. An ultrasonic diagnosis apparatus including an ultrasonic probe having a plurality of vibrating elements, the plurality of vibrating elements having electromechanical coupling coefficients that vary in accordance with the magnitude of a bias voltage supplied from a bias voltage supply unit, an ultrasonic image constructing unit for constructing an ultrasonic image based on a reflection echo signal received from the ultrasonic probe, and a display unit for displaying the ultrasonic image, the ultrasonic diagnosis apparatus comprising:

an operation unit that determines what percentage, in a predetermined range of percentages, of collapse voltage should be set as a bias voltage, wherein the collapse voltage is obtained from a histogram including collapse voltages of the plurality of vibrating elements distributed with respect to frequency of the collapse voltages;

a calculation unit for calculating the magnitude of the bias voltage, the magnitude of the bias voltage being lower than a magnitude of the collapse voltage obtained from the histogram, wherein the operation unit sets the calculation unit so that the percentage of the collapse voltage is set as the magnitude of the bias voltage; and a control unit for controlling the magnitude of a bias voltage which is supplied to the plurality of vibrating elements from the bias voltage supply unit.

2. The ultrasonic diagnosis apparatus according to claim 1, further comprising:

a storage unit in the ultrasonic probe.

3. The ultrasonic diagnosis apparatus according to claim 1, further comprising:

a storage unit, wherein the control unit causes the calculation unit to calculate, as the magnitude of the bias voltage, a value that is equal to or less than an average of the collapse voltages of the vibrating elements, and causes the storage unit to store the calculated magnitude of the bias voltage in the storage unit.

4. The ultrasonic diagnosis apparatus according to claim 1, further comprising:

a storage unit, wherein the control unit causes the calculation unit to calculate the magnitude of the bias voltage every vibrating element of the plural vibrating elements so that the magnitude of the bias voltage is equal to or less than a pre-measured collapse voltage, and causes the storage unit to store the calculated magnitude of the bias voltage in the storage unit.

5. The ultrasonic diagnosis apparatus according to claim 1, further comprising:

a storage unit, wherein the control unit causes the calculation unit to calculate the magnitude of the bias voltage on the basis of one of voltages which are equal to or less than all collapse voltages of the plural vibrating elements, and causes the storage unit to store the calculated magnitude of the bias voltage therein.

6. The ultrasonic diagnosis apparatus according to claim 1, further comprising:
a storage unit; and
a collapse voltage measuring unit for measuring the collapse voltage with time lapse,
wherein the control unit causes the calculation unit to calculate the magnitude of the bias voltage so that the magnitude of the bias voltage is not more than a collapse voltage measured by the collapse voltage measuring unit, and causes the storage unit to store the calculated magnitude of the bias voltage.

7. The ultrasonic diagnosis apparatus according to claim 1, further comprising:
a storage unit,
wherein the control unit causes the calculation unit to calculate the magnitude of the bias voltage so that the magnitude of the bias voltage is not more than a collapse voltage measured in accordance with the type of the vibrating elements, and causes the storage unit to store the calculated magnitude of the bias voltage in the storage unit.

8. The ultrasonic diagnosis apparatus according to claim 1, further comprising:
a storage unit,
wherein the control unit causes the calculation unit to calculate the magnitude of a bias voltage which is different every channel constructed by the plural vibrating elements, and causes the storage unit to store the calculated magnitude of the bias voltage in the storage unit.

9. The ultrasonic diagnosis apparatus according to claim 1, further comprising:
a plurality of channels, each of the plurality of channels comprising at least one vibrating element of the plurality of vibrating elements; and
a collapse voltage measuring unit for measuring the collapse voltage of one vibrating element of the plurality of vibrating elements,
wherein the calculation unit calculates as the magnitude of the bias voltage, a value that is less than the collapse voltage of the one vibrating element.

10. The ultrasonic diagnosis apparatus according to claim 1, further comprising:
a plurality of channels, each of the plurality of channels comprising at least one vibrating element of the plurality of vibrating elements,
wherein the magnitude of the bias voltage is distributed across the plurality of channels, a weight for the magnitude of the bias voltage being set for every channel.

11. The ultrasonic diagnosis apparatus according to claim 10, further comprising:
a bias voltage supply unit that increases the weight for the magnitude of the bias voltage of at least one channel located at a center channel of the plurality of channels, and reduces the weight for the magnitude of the bias voltage for at least one channel located away from the center channel of the plurality of channels.

12. The ultrasonic diagnosis apparatus according to claim 1, further comprising:
wherein the collapse voltage calculated by the calculation unit is an average value of magnitudes of collapse voltages obtained from every at least two vibrating elements of the plurality vibrating elements.

13. The ultrasonic diagnosis apparatus according to claim 1, further comprising:
a capacitance measuring unit for measuring a capacitance value of the vibrating elements,
wherein the calculation unit traces a relationship between the magnitude of a bias voltage supplied to a vibrating element by the bias voltage supply unit and the capacitance value of a vibrating element measured by the capacitance measuring unit, thereby extracting a capacitance-voltage curve (CV curve) for the vibrating element, and
wherein the collapse voltage of the vibrating element is represented by a point at which the increase of the capacitance value is stopped on the CV curve.

14. The ultrasonic diagnosis apparatus according to claim 13,
wherein the calculation unit extracts a CV curve for at least two of the vibrating elements, determines the collapse voltages from the CV curve for each of the respective vibrating elements, calculates an average value of the collapse voltages determined for the at least two vibrating elements, and calculates as the magnitude of the bias voltage a value that is equal to or less than the average value of the collapse voltages determined for the at least two vibrating elements.

15. An ultrasonic diagnosis apparatus having an ultrasonic probe, the ultrasonic probe having a plurality of vibrating elements, the plurality of vibrating elements having electromechanical coupling coefficients that vary in accordance with the magnitude of a bias voltage supplied from a bias voltage supply unit, an ultrasonic image constructing unit for constructing an ultrasonic image based on a reflection echo signal received from the ultrasonic probe, and a display unit for displaying the ultrasonic image, the ultrasonic diagnostic apparatus comprising:
a storage unit for storing a plurality of collapse voltages of the plurality of vibrating elements, each vibrating element having a corresponding collapse voltage;
an operation unit that determines what percentage, in a predetermined range of percentages, of the collapse voltage should be set as a bias voltage,
wherein the collapse voltage is obtained from a histogram including collapse voltages of the plurality of vibrating elements distributed with respect to frequency of the collapse voltages; and
a control unit for calculating the magnitude of the bias voltage, the magnitude of the bias voltage being lower than a magnitude of the collapse voltage obtained from the histogram, and for controlling the magnitude of a bias voltage which is supplied to the plurality of vibrating elements from the bias voltage supply unit.

16. An ultrasonic probe comprising:
a plurality of vibrating elements having electromechanical coupling coefficients that vary in accordance with a bias voltage supplied from a bias voltage supply unit;
a storage unit for storing information regarding the vibrating elements,
wherein the storage unit stores a plurality of collapse voltages of the vibrating elements, each vibrating element having a corresponding collapse voltage; and
an operation unit that determines what percentage, in a predetermined range of percentages, of the collapse voltage should be set as a bias voltage,
wherein the collapse voltage is obtained from a histogram including collapse voltages of the plurality of vibrating elements distributed with respect to frequency of the collapse voltages; and
a calculation unit for calculating the magnitude of the bias voltage, the magnitude of the bias voltage being lower than a magnitude of the collapse voltage obtained from the histogram.

17. A method of constructing an ultrasonic image using an ultrasonic image apparatus, the ultrasonic image apparatus including an ultrasonic probe having a plurality of vibrating elements, the plurality of vibrating elements having electro-mechanical coupling coefficients that vary in accordance with a magnitude of a bias voltage supplied from a bias voltage supply unit, an ultrasonic image constructing unit for constructing the ultrasonic image based on a reflection echo signal received from the ultrasonic probe, and a display unit for displaying the ultrasonic image, the method comprising:

determining, by an operation unit, what percentage, in a predetermined range of percentages, of collapse voltage should be set as a bias voltage, wherein the collapse voltage is obtained from a histogram including collapse voltages of the plurality of vibrating elements distributed with respect to frequency of the collapse voltages;

calculating, by a calculation unit, the magnitude of the bias voltage, the magnitude of the bias voltage being lower than a magnitude of the collapse voltage obtained from the histogram, wherein the percentage of the collapse voltage is set as the magnitude of the bias voltage; and controlling, by a control unit, the magnitude of a bias voltage which is supplied to the plurality of vibrating elements from the bias voltage supply unit.

* * * * *